(12) United States Patent
Ward

(10) Patent No.: US 9,027,420 B1
(45) Date of Patent: May 12, 2015

(54) SPECIMEN COLLECTION, TREATING, AND TRANSPORTING SYSTEM

(76) Inventor: N. Robert Ward, Bothell, WA (US)

(*) Notice: Subject to any disclaimer, the term of this patent is extended or adjusted under 35 U.S.C. 154(b) by 367 days.

(21) Appl. No.: 13/308,320

(22) Filed: Nov. 30, 2011

(51) Int. Cl.
*G01N 1/02* (2006.01)

(52) U.S. Cl.
CPC ........................... *G01N 1/02* (2013.01)

(58) Field of Classification Search
CPC .............. G01N 1/04; G01N 1/02; G01N 1/08
USPC ........................ 73/864.71; 422/400
See application file for complete search history.

(56) References Cited

U.S. PATENT DOCUMENTS

| | | | | |
|---|---|---|---|---|
| 2,835,246 | A * | 5/1958 | Boettger | 600/570 |
| 5,266,266 | A * | 11/1993 | Nason | 422/411 |
| 6,991,898 | B2 * | 1/2006 | O'Connor | 435/4 |
| 7,247,273 | B2 * | 7/2007 | Nunes et al. | 422/520 |
| 8,075,850 | B2 * | 12/2011 | Sangha et al. | 422/406 |
| 2004/0042934 | A1 * | 3/2004 | Nunes et al. | 422/100 |
| 2005/0084842 | A1 * | 4/2005 | O'Connor | 435/4 |
| 2007/0166198 | A1 * | 7/2007 | Sangha et al. | 422/99 |
| 2011/0004122 | A1 * | 1/2011 | Sangha | 600/572 |

OTHER PUBLICATIONS

Evancho, G.M., et al., "Microbiological Monitoring of the Food Processing Environment," in F.P. Downes et al. (eds.), Compendium of Methods for the Microbiological Examination of Foods, 4th ed., American Public Heath Association, 2001, pp. 25-30.
Wiczer J., and K. Lee, "A Unifying Standard for Interfacing Transducers to Networks—IEEE-1451.01," presented at ISA Expo 2005: Automation, Control, and Inspiration, Chicago, Illinois, Oct. 25-27, 2005, 10 pages.

* cited by examiner

*Primary Examiner* — Peter Macchiarolo
*Assistant Examiner* — Nathaniel Kolb
(74) *Attorney, Agent, or Firm* — Christensen O'Connor Johnson Kindness PLLC

(57) ABSTRACT

A swab for obtaining a biological surface sample has a shaft extending from a first side of a cap. A first test tube can be coupled to the first side of the cap in a detachable watertight fit, to enclose the swab. A second tube can be coupled to a second side of the cap in a manually detachable watertight fit. The first tube or the swab can include a collection solution; the second tube can be used as a handle to extend the reach of the swab when the first tube is detached; and the second tube can contain an enrichment broth and/or developer solution for the collected sample.

8 Claims, 6 Drawing Sheets

SPECIMEN COLLECTION, TREATING, AND TRANSPORTING SYSTEM

BACKGROUND

Sampling of surfaces is routinely done by companies that need to control the type and level of microorganisms and non-living contaminants (e.g., allergens) in their production environment. For example, in many food companies surface sampling is done in an effort to reduce the possibility of pathogens (disease-causing organisms) and/or spoilage organisms from environmental sources entering food products during production. *The Compendium of Methods for the Microbiological Examination of Foods* (4$^{th}$ edition), at pp. 25-30 discusses the rationale for environmental sampling, strategies for collecting a sample, and commonly used methods for collecting a sample. Another system is described in U.S. Pat. No. 5,266,266. Reference may be had to these publications and the documents referred to therein (including references cited) for representative known sampling systems and devices.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with one aspect of the present invention, a sampling device is provided having a two sided cap. The cap can act as a coupling between different sampling system components.

The shaft of a sampling swab can be fitted into a receiving area on the first side of the cap and secured therein. The receiving area for the shaft of the swab can accommodate shafts of different thicknesses for different sampling requirements.

A first test tube can be joined to the cap on the first side to enclose the swab and maintain sterility of the swab. The first test tube can be loaded with a collection solution before use. During sampling, the cap is held by the analyst, the first test tube is removed, and the sample is collected by scrubbing absorbent material of the swab with a collection solution on the surface. Alternatively, the analyst may join a second test tube or an extension device to the second side of the cap to improve the holding and reach of the analyst while collecting a sample. After the sample has been collected, the first test tube can be returned to the first side of the cap.

In accordance with other aspects of this invention, the second test tube on the second side can be loaded with a culturing broth appropriate for the detection of the target organism(s) to facilitate sequential sample collection and processing. After the first test tube has been disconnected from the first side and the sample collected, the second test tube can be disconnected from the second side, and the swab can be conveniently placed into the second test tube, whereupon both tubes can be reconnected to the cap.

After the sample is collected, the first test tube and/or the second test tube can be accessed by the analyst as needed to perform one or more tests.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
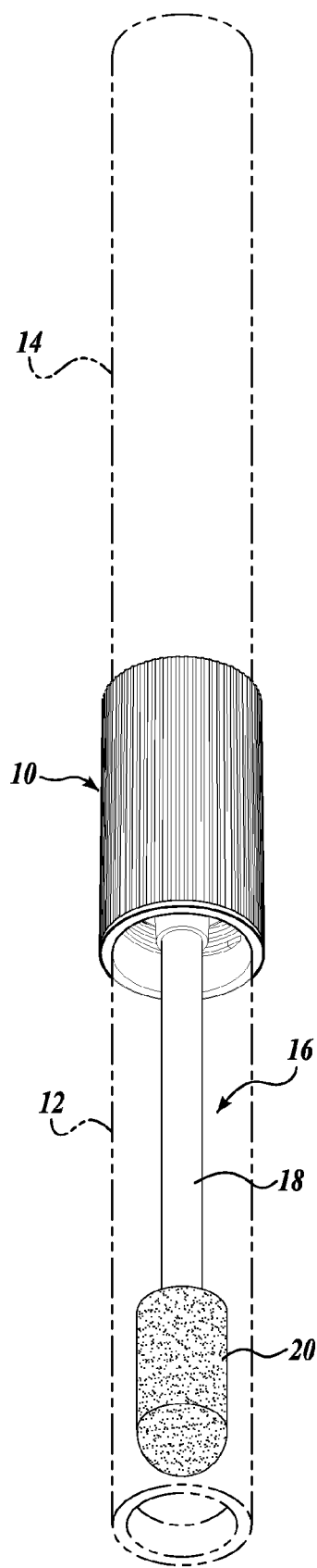
FIG. 1 is a bottom perspective of a component of a specimen collection system in accordance with the present invention, with additional components shown in broken lines.

Typically, biological surface samples are collected using swabs or sponges that are hydrated with specially formulated collection solutions. The collection solution usually has two purposes: (i) to neutralize residual sanitizers that may be left behind with the cleaning process; and (ii) to maintain the viability of microbial cells collected by the swab or sponge during sampling.

Microorganisms residing on a surface may be part of a biofilm that is firmly attached to the surface. To get an accurate determination of the presence and/or the level of microorganisms on the surface, it is necessary to disrupt and lift the biofilm with vigorous scrubbing using a swab or sponge. Swabs are effective tools for sampling smaller areas, especially those samples that are in difficult to access areas, such as production equipment. The food industry continues to uses swabs that were originally designed for collection of clinical samples (e.g., throat or vaginal swabs). While the thin and bendable shaft of this type of swab is helpful for reaching into a tight area, it is difficult to use these swabs to vigorously scrub a surface to lift a biofilm. Also, these swabs are generally available with small tips made of Dacron, cotton, or alginate. The small size of the tip limits the area that can easily and effectively be scrubbed while collecting a sample.

Sponges, held by a gloved hand, sterile forceps or built onto a removable handle, are employed to collect larger surface samples. After a sample is collected, these sponges are usually transported back to a laboratory in a sterile sample bag with a wire closure. These sample bags are bulky, difficult to manipulate without accidentally introducing-contaminants and may leak during transportation back to the laboratory and in sample processing in the laboratory.

A preferred device in accordance with the present invention can utilize a member, such as a test tube, that can function as a handle to enhance vigorous scrubbing of the surface, and/or to improve collection of a remote sample, and/or to lessen the possibility of the sampled area being contacted by the hand of the person collecting the sample which could cause contamination. In an alternative form, an extended handle, such as an extension pole, can be attached to the sampling device so that very remote areas, such ceilings, drains and tanks, can be sampled.

The organisms that are present on the surface may be in an injured state caused by application of a sanitizer, or because they reside in a nutrient deplete and/or dry environment. The microbiologist collecting the sample needs to be aware that these stressed organisms could die if not properly handled when and after the sample is collected. It should be noted that even though the microorganisms are in a stressed state, these organisms, if introduced from the environment into a food product, might recover from injury and begin to grow, resulting in a danger to the consumer.

After sampling of the surface, the collection device is sent to a laboratory for further processing, leading to information about the presence of certain types of microorganisms (such as *Listeria monocytogenes, Escherichia coli* or *Salmonella* species) or levels of microorganisms on the sampled area. A common approach is to collect the sample, transport the sample to the laboratory using a cooler with a frozen blue ice pack to keep the sample at a temperature of 4 to 8° C., and then process the sample upon receipt by the laboratory. If the sample is collected on a Friday, it is possible that the sample may not be processed by the laboratory until Monday. Similarly, if the company uses an external contract testing laboratory, the sample may need to be shipped overnight.

The ideal solution for collecting a sample ("collection broth" or "collection solution") is one that can neutralize residual sanitizer, can support the viability of injured organisms collected by the swab or sponge, and is non-toxic so that if it is left on the sampled surface (perhaps a food contact surface) that there will not be harmful consequences to the consumer if this material comes in contact with the food. For example, it would be best to utilize a collection solution that is capable of neutralizing all types of commonly used sanitizers (including quaternary ammonium, phenolic, chlorine and peracetic acid sanitizers), would provide an environment that has a neutral pH and can maintain osmotic balance, would supply a nutrient(s) that can aid the injured cells in their recovery and is not dangerous to the consumer. A collection solution that is not dangerous to the consumer is one that does not contain allergens, antibiotics, heavy metals and metal salts, and potentially toxic and/or cancer causing substances.

For detection of a bacterial pathogen in an environmental sample, the swab or sponge is processed by first placing it into a culturing broth (typically called an "enrichment broth"). If a pathogen is present in an environmental sample, it is often present at a very low level (perhaps only 1 to 2 cells) and it is in an injured state. The enrichment broth has three purposes. The first is to help a potentially injured pathogenic cell to recover from its injury so that it can initiate growth. The second purpose is to support the unrestricted growth of the pathogen so that it reaches a high level for detection. The third purpose is to completely inhibit or slow the growth of microorganisms ("competitor" organisms) that may compete for nutrients in the culturing broth and interfere with the detection test. The ideal enrichment broth is one that optimizes recovery of highly injured organisms, supports their unrestricted growth and totally suppresses the growth of competitor organisms.

Below is a table showing commonly used enrichment broths for growing *Listeria* as the first step in a detection procedure of this organism. The potentially hazardous or dangerous materials in these enrichment broths are shown in this Table. These agents are included in these broths for the purpose of inhibiting or suppressing the growth of non-*Listeria* organisms while permitting the growth of the target organism.

| Type of Enrichment Broth | Potentially Hazardous Or Dangerous Materials Added to the Broth | Hazard Type |
| --- | --- | --- |
| UVM Modified Listeria Enrichment Broth | Nalidixic Acid; Acriflavine | Nalidixic acid has potential to cause convulsions and hyperglycemia; Acriflavine may cause birth defects |
| Paradigm Diagnostics Listeria Indicator Broth | Nitrofurantoin; Cycloheximide; Naldixic Acid; Ceftazidime; Phosphomycin; Polymyxin E | Nitrofurantoin is toxic to kidneys and nervous system; Cycloheximide is a suspected teratogen; Ceftazidime, phosphomycin, and polymyxin E may cause allergic reaction |
| Demi Fraser Broth | Nalidixic Acid; Acriflavine; Lithium Chloride | Lithium chloride is a possible teratogen; is mutagenic |
| Listeria Enrichment Broth | Cycloheximide; Acriflavine; Nalidixic Acid | See Above |

As compared to the practice described above of collection, transport, and delayed testing of a sample, the present invention provides a system for detecting a pathogen in an environmental sample in a way that allows the analyst to initiate enrichment of the sample immediately or very soon after the sample is collected. For example, a test tube used as a handle can be loaded with an enrichment broth and/or developer solution used in the performance of a test on the collected surface sample. With rapid initiation of the enrichment process, there will be an increased likelihood that the injured organism will be recovered and detected. The preferred approach is to place the swab or sponge immediately into the enrichment broth after sample collection. A second benefit of starting the enrichment step right after sample collection is that the target organism may be detected earlier since the test is started earlier. In this case, it may not be desirable to transport the sample in a cold environment. Rather, growth may be initiated by incubation at ambient temperatures while the processed sample is brought to the laboratory and then placed in an incubator at temperatures of 30° C. or 35° C. (It should be noted that recovery of injured organism may be enhanced by a short incubation time at a temperature below normal incubation temperature, such as room temperature.) A third benefit of starting the sample enrichment step immediately is convenience. The immediate initiation of sample processing eliminates further handling in the laboratory.

The best case is one where the collection solution is the same as the enrichment solution. In most cases, this is not possible as the sample collection broth needs to be free of toxic materials so that it can safely be used on product contact surfaces. Many enrichment broths contain components such as heavy metals, antibiotics or other materials that may be toxic to humans if ingested.

For *Listeria* sampling and testing, it would not be appropriate to use a swab or sponge hydrated with UVM Broth, for example, to collect an environmental sample because the UVM Broth contains potentially hazardous components (acriflavine and nalidixic acid) that should not be placed and left on a production surface. Also, the UVM broth does not contain agents to neutralize residual sanitizer on the production surface. A similar situation exists for the detection of *E. coli* serotype 0157 in environmental samples. It has been shown that addition of the antibiotics acriflavin or novobiocin to Trypticase Soy Broth (TSB) is advantageous for sample enrichment. Again, it would be potentially dangerous to collect an environmental sample with a swab or sponge hydrated with TSB+acriflavin or TSB+novobiocin.

One type of sampling device is available that allows a broth to be added to a swab after the sample is collected. "Insite," a product available from Hygiena, Camarillo, Calif., utilizes a specimen test unit described in U.S. Pat. No. 5,266,266. This specimen test unit uses a deformable reagent chamber with a break-off nib at the rear end of a hollow-shafted swab that allows a culture broth to flow from the reagent chamber, down through the shaft and to the swab tip when the user breaks the nib. One limitation of this technology is that the user is restricted to culture broths supplied by the manufacturer. This could be problematic if the company does not offer the broth desired by the customer or the culture broth has a very short shelf-life because of instability in one or more components of the broth. The preferred approach would be one where the user would have the option to utilize a culturing broth supplied by the manufacturer or could add their desired broth to the device just before sample collection. The second disadvantage of the Insite specimen test unit is that, once the culture broth is added to the swab, only the organism(s) capable of growth in this broth (for example, a *Listeria* specific enrichment broth such as that used in the Insite product) will be able to grow. *E. coli* or *Salmonella*, for example, would not grow in a broth formulated to grow *Listeria*. The preferred approach is one where the user has the capability to perform tests for different types of bacteria (for example *Listeria, Salmonella* and/or *E. coli*) from a single sampling device. Finally, enzyme immunoassays that are routinely used to detect pathogenic bacteria in enrichment broths require that the enrichment broth be heated to, or near, boiling temperatures to kill the microorganisms in the broth prior to running the assay. One complication of the heat kill step is that a portion of the broth needs to be transferred to a separate container (generally a test tube) prior to the heat kill step in order to maintain viable (non heat treated) organisms for later confirmation work if the immunoassay is positive for the pathogen. A preferred approach is to utilize a device whereby one part of the device is heat treated, while the other remains unheated (or below lethal temperature) so that confirmation work can be performed on the living cells held in the unheated portion of the device at a later date.

In addition to the critical use of a sampling device for collecting microorganisms on a surface, there is an equally important need for a sampling device that can collect substances such as an allergen (for example soy, peanut, wheat, milk), protein, ATP, antibiotic, and/or carbohydrate on a surface. The presence of one of these substances may indicate that a surface has not been adequately cleaned or that this surface is dangerous if one of these components (for example an allergen) unknowingly enters a product that should be free of this substance. An approach for a chemical contaminant would be similar to that used for microorganism sampling and testing. For example, if a test is conducted for a protein on a surface, a swab would be used to collect the sample and then the swab would be placed into a developer solution (for example, the Bicinchoninic acid (BCA) assay) that changes color when proteins are present.

In situations where a sample is taken in a production environment, it is important that all components of a sampling device that are brought into the production area are accounted for and brought out. The reputation of a company, for example, would be adversely impacted if a user collecting a sample accidentally lost track of a component of the sampling device and a consumer encountered this part when consuming the product, such as a food or pharmaceutical. A preferred device is one where all components of the device are part of an integrated unit. Such an integrated device would minimize the likelihood of a part not being accounted for because that part was critical to performing the test or because it would be obvious to the sample collector that the part was missing from the integrated unit.

Inappropriate materials and practices used for sample collection and sample processing can cause false negative results where the presence of a pathogenic organism is missed. This could lead to a false conclusion that the manufacturing area is safe for production.

The preferred device would enhance sample collection by assisting the analyst in the collection of a representative sample. The favored device would improve the ability of the analyst to firmly press down on a sampling surface and to reach into a remote testing area. This device would also enhance the ability of the analyst to collect a surface sample with minimal opportunity for accidental contamination. The preferred design would permit the use of swabs with shafts of different thicknesses to accommodate a variety of sampling challenges from reaching into tight spaces, where a thin shaft would be most beneficial, to a thicker shaft that would facilitate more vigorous scrubbing of larger surfaces. Such a device would allow the user to collect a sample that could be analyzed for one or more target organisms or substances and would facilitate post-collection processing of the sample, such as heat treatment prior to performing an immunoassay.

Moreover, a need exists for an improved device that allows the analyst to (i) collect a surface sample using a swab hydrated with a non-toxic collection solution, (ii) initiate sample processing immediately or soon after the sample has been collected using an enrichment broth and/or developer solution and (iii) access collection broth or enrichment broth contained in the device for further analyses such as confirmation of a target microorganism.

With reference to FIG. 1, an embodiment of a sampling device in accordance with the present invention has two sided cap 10 which can act as a coupling between other components, such as a bottom test tube or vial 12 and an upper test tube or vial 14. A sampling swab 16 projects from a first side of the cap (downward as viewed in FIG. 1) with its slender but sturdy shaft 18 leading to the absorbent sample-collecting material 20. In a preferred embodiment the sample collecting material is a dense sponge that will withstand vigorous scrubbing without damage or shedding, such as a polyurethane foam, and the shaft is sturdy but nonbrittle to allow significant force to be applied. Swab 16 is fully enclosed in the bottom test tube 12, and the open end of the tube is joined to the first side of the cap in a manually detachable but watertight fit. The upper test tube 14 extends oppositely and has its open end joined to the cap by a separate manually detachable but watertight fit.

Figure 2:
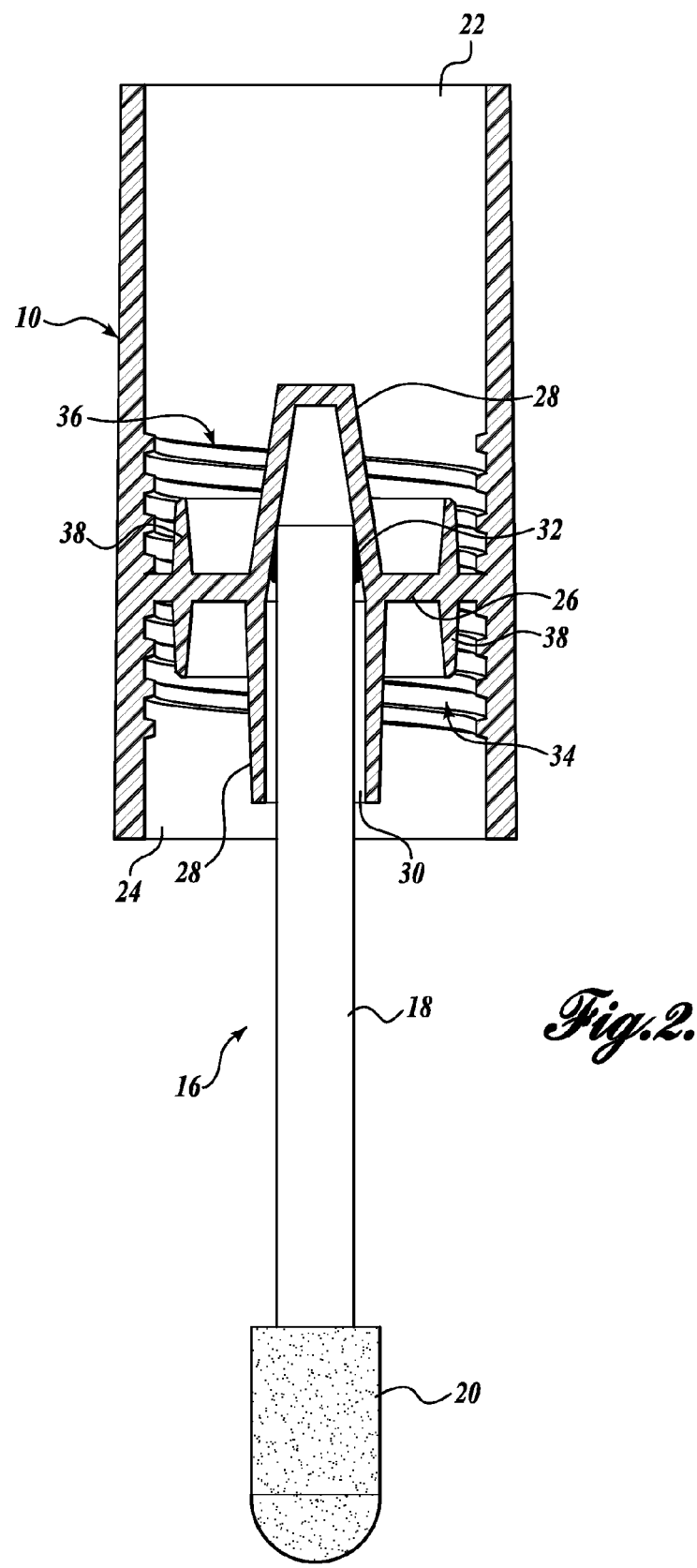
FIG. 2 is an enlarged vertical section through the solid line component of FIG. 1.

With reference to FIG. 2, the cap 10 can have a cylindrical outer periphery, most of which is a hollow shell. The exterior can be ribbed for reliable gripping by a sampling technician. The top 22 is open to the interior of the cap, as is the bottom 24. However, the top and bottom are sealed from each other by an integral central hub portion which includes a horizontal disc section 26 that leads to an axial socket 28. The socket is open at the first side of the cap (the "bottom") and closed at the second side (the "top"). The bore 30 of the socket forms a receiving area for a considerable length of the top portion of the shaft 18. The upper part of the bore tapers gradually inward so that the shaft is tightly seated therein during assembly. A small amount of hot melt glue or other non-toxic adhesive 32 can be used to firmly secure the swab in position. A swab with a narrower shaft will seat higher in the socket but still be firmly wedged therein, whereas a swab with a broader shaft will seat lower. Consequently, the cap is adapted for use with swabs having shafts of different diameters.

As noted above, the cap and the associated test tubes have manually detachable but watertight fits. In the illustrated embodiment, the fit is by mating, snug screw threads. The cap has a first set 34 of internal threads adjacent to but below the hub portion, and a second set 36 adjacent to but above the hub. Each test tube has mating external threads along is open end portion. At each side the fit is enhanced by a continuous annular skirt 38 that is spaced a short distance inward from the threaded portion of the cap, less than the thickness of the wall of a test tube along its open end portion. As the cap is manually screwed on to the corresponding tube, or vice versa, the open end portion of the tube is engaged between the inner periphery of the outer shell of the cap and the adjacent skirt for a reliable tight fit.

Figure 3:
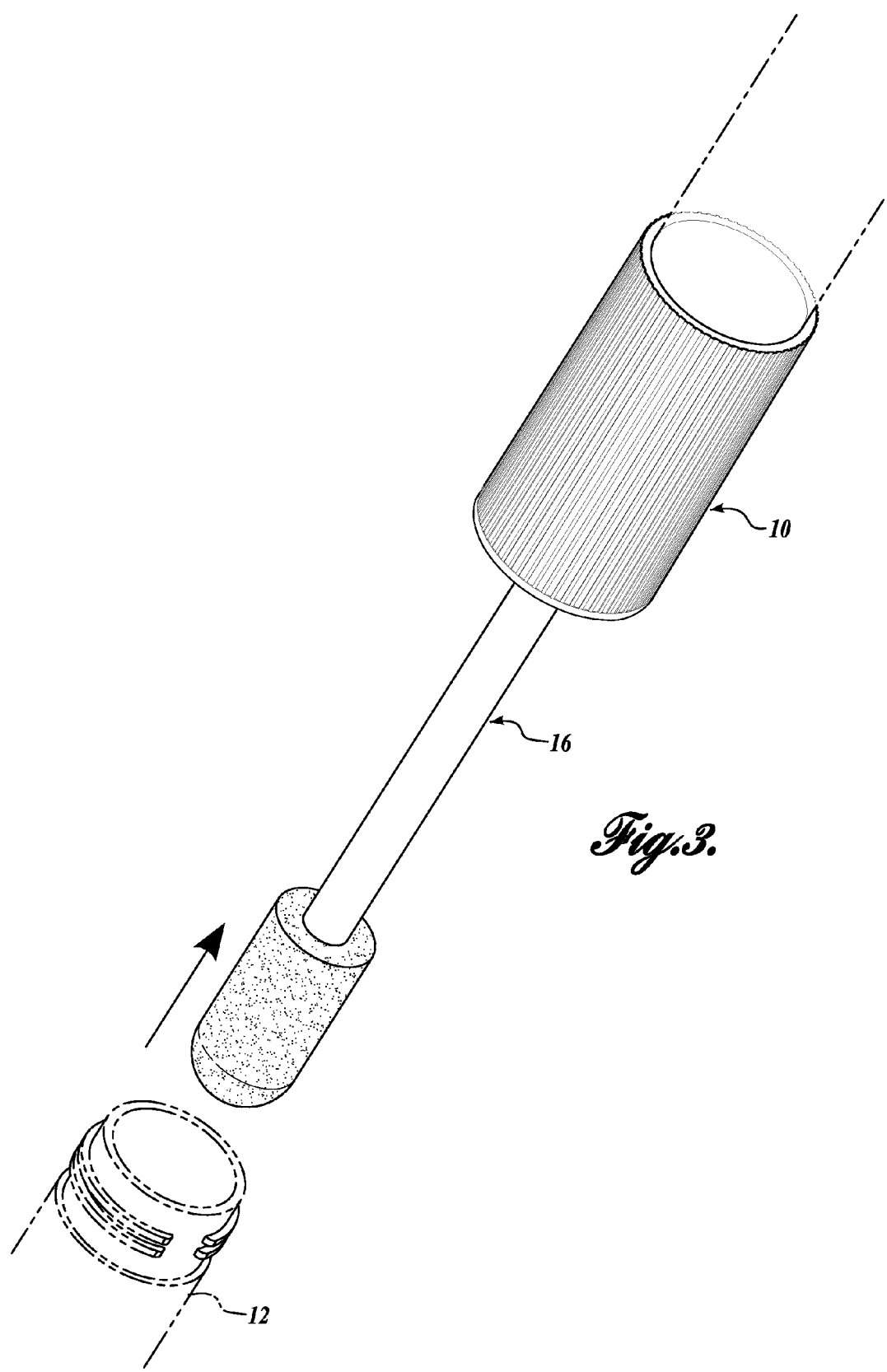
FIG. 3 is a diagrammatic top perspective of the FIG. 1 components with parts in different positions, illustrating a first step in a representative sampling procedure.
Figure 4:
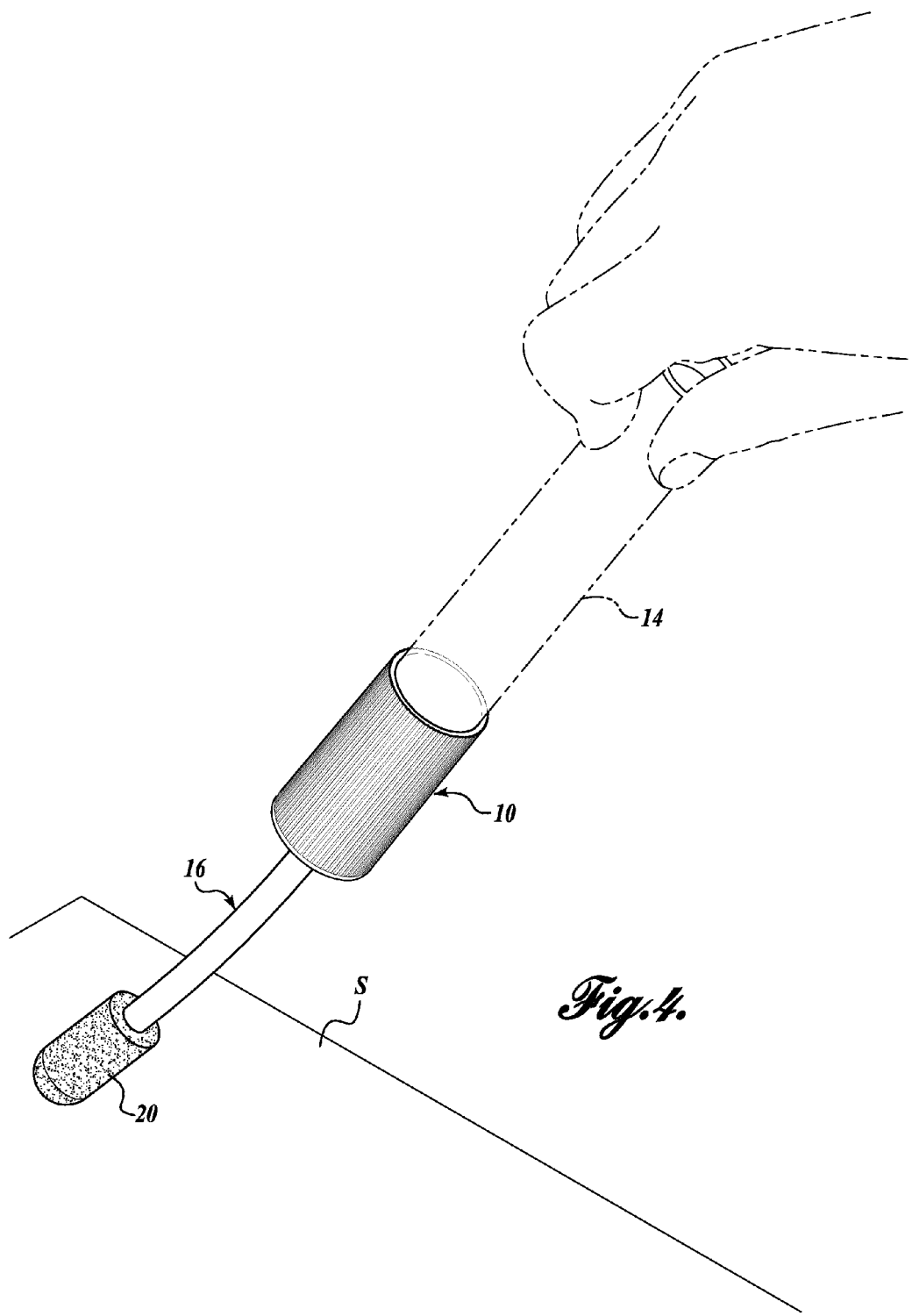
FIG. 4 is a diagrammatic top perspective corresponding to FIG. 3 illustrating a subsequent step in the representative sampling procedure.

In one embodiment, the absorbent swab material 20 is hydrated with a collection solution, such as DIE Neutralizing Broth when testing for *Listeria*. As represented in FIG. 3, the lower test tube 12 is uncoupled from the cap 10 and its swab 16. As seen in FIG. 4, the surface S to be sampled can be scrubbed with the absorbent material 20. The upper tube 14 acts as a convenient extension handle to increase the reach of the swab. Another benefit is increased leverage for applications that require or benefit from vigorous scrubbing, and still another benefit is spacing the hand of the user farther away from the surface being sampled and the surrounding environment to avoid physical contact with the hand of the user that could cause contamination. If greater reach is desired, the top of the cap 10 can be coupled to a longer extension tube or handle having the same mating threads as the upper test tube.

Figure 5:
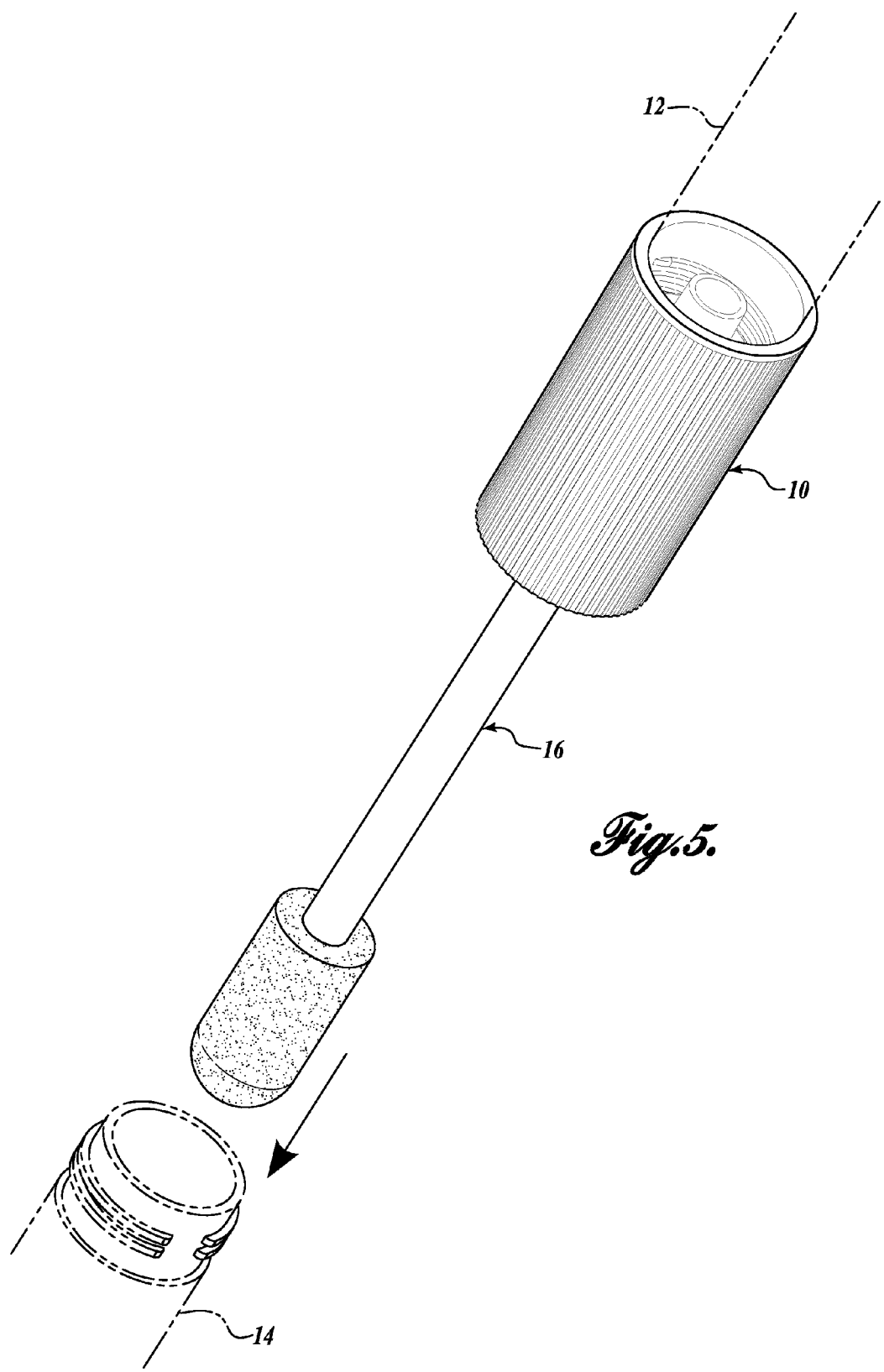
FIG. 5 is a diagrammatic top perspective corresponding to FIGS. 3 and 4 illustrating a later step in the representative sampling procedure.

In accordance with another aspect of the present invention, the second test tube 14 can be loaded with a desired enrichment broth, for example, UVM Broth, and/or a developer solution that can cause detection of ATP, protein, antibiotic, or allergen on a surface. In this case, when the sample scrub is completed, the second test tube 14 is uncoupled from the second side of the cap and the swab is placed into the second test tube, as represented in FIG. 5. The second tube is then coupled to the first side of the cap, and the other tube 12 can be coupled to the second side. In this way, the enrichment broth is applied to the sample collected by the swab without delay, despite the fact that different sampling and enrichment solutions/broths are used. The device can be preloaded at the time of manufacture, or the user can load the assembly with whatever solutions are appropriate for the particular test to be conducted. Also, all of the sampling pieces will be secured together and nothing will be inadvertently left behind.

Figure 6:
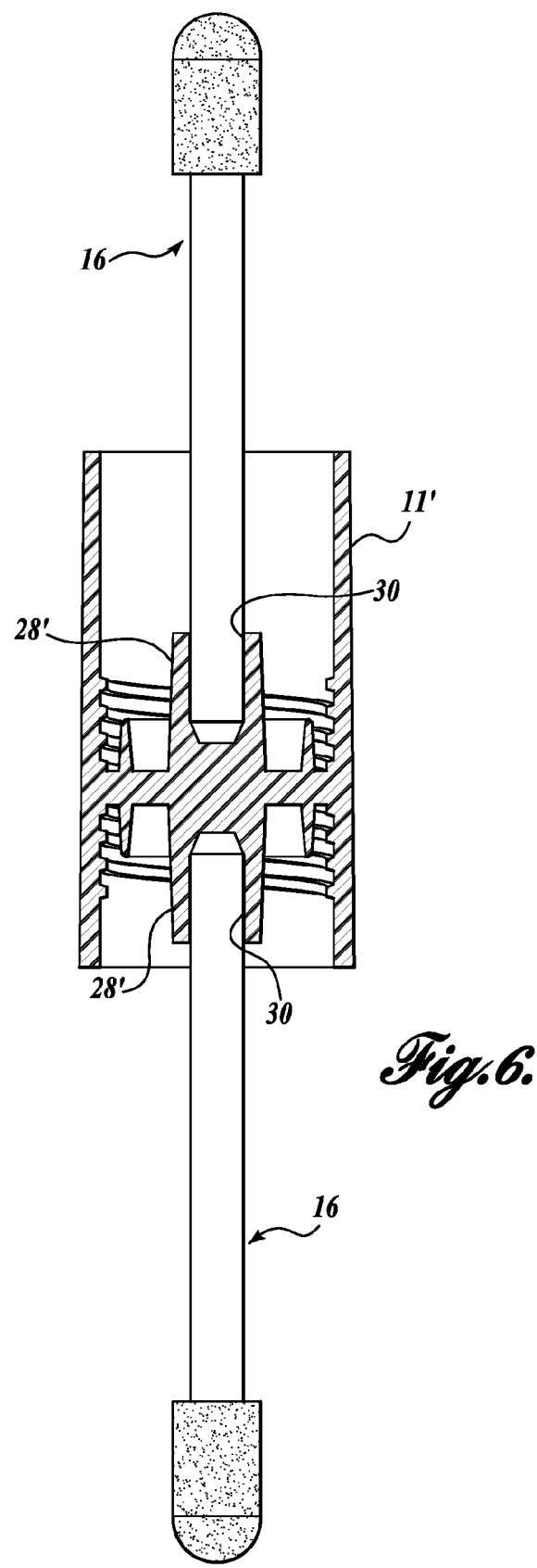
FIG. 6 is an enlarged vertical section through a modified component of the general type shown in FIG. 1.

In the modified embodiment shown in FIG. 6, the hub portion of the two sided cap 11' has a socket member 28' with first and second (top and bottom) axial shaft-receiving bores 30'. A swab 16 can be placed on both sides prior to coupling of the test tubes. This configuration gives the technician/analyst the opportunity to grasp the test tube on one side while removing the test tube on the other side, collect a sample with the swab on that side and returning the test tube. When this first sample is collected, a second sample can be collected using the sequence described for the first swab. In this procedure, the enrichment solution and/or developer solution can be added later, but preferably very soon after the samples are collected.

While illustrative embodiments have been illustrated and described, it will be appreciated that various changes can be made therein without departing from the spirit and scope of the invention.

The embodiments of the invention in which an exclusive property or privilege is claimed are defined as follows:

1. A microbiological sampling kit for collecting suspected microorganisms from a surface, comprising:
    a hollow cap having a first side and a second side separated from each other, the two cap sides not being in communication;
    a sample-collecting swab having a shaft extending from only the first cap side and a sample-collection material portion carried by the shaft, the second cap side being devoid of any sample collecting component;
    a first test tube coupled to the first cap side in a manually detachable watertight fit and enclosing the swab so as to seal the interior of the first test tube and the swab from the surrounding atmosphere, the first test tube being manually detachable from the first cap side to expose the swab for collection of a sample for microbiological analysis, the first test tube being constructed for optional attachment to the second cap side in a manually detachable watertight fit;
    a second test tube coupled to the cap second side in a manually detachable watertight fit and extending from the cap away from the first test tube and the swab, the second test tube being constructed for optional attachment to the first cap side in a manually detachable watertight fit; and
    a quantity of enrichment broth contained in the second test tube for supporting recovery or growth of a microorganism sample of a suspected microorganism collected by use of the swab by uncoupling the cap second side from the second test tube and coupling the cap first side to the second test tube to enclose the swab in the second test tube, sealing the interior of the second test tube and the swab from the surrounding atmosphere, and exposing the swab and sample collected thereby to the enrichment broth.

2. The microbiological sampling kit defined in claim 1, in which the cap has an internal socket including an elongated bore for receiving an end portion of the swab shaft and for securing of the shaft therein.

3. The microbiological sampling kit defined in claim 1, in which the first side of the cap has internal threads, the first test tube having external threads coupling the first test tube to the first cap side in the manually detachable watertight fit, and in which the second side of the cap has internal threads, the second test tube having external threads coupling the second test tube to the second cap side in the manually detachable watertight fit.

4. The microbiological sampling kit defined in claim 1, in which the swab is hydrated with a collection solution prior to coupling to the first side of the cap.

5. An assembly for a biological surface sampling system for collecting suspected microorganisms from a surface, said assembly comprising:
    a cap in the form of a hollow shell having a first side and a second side separated from each other, the two sides not being in communication;
    a sample-collecting swab carried by the cap and having a shaft extending away from the first side of the cap to a sample-collection material portion of the swab, the second cup side being devoid of any sample collecting component;

a first test tube;

a second test tube, each of said tubes having a closed end and an open end, each of the first and second sides of the cap and each of the open ends of the first and second tubes being constructed and arranged for coupling together in a manually detachable watertight fit, whereby the open end of each of the tubes is adapted for coupling to either side of the cap, the open end of the first tube being coupled to the cap first side with the first tube in combination with the cap enclosing the swab so as to seal the interior of the first test tube and the swab from the surrounding atmosphere but with the first tube being manually detachable from the cap to expose the swab for use in collection of a sample, the open end of the second tube being coupled to the second side of the cap and extending from the cap second side in a direction away from the first tube and swab so as to seal the interior of the second test tube from the surrounding atmosphere but being manually detachable therefrom to receive the swab and couple to the first cap side after a sampling collection procedure; and a quantity of enrichment broth preloaded in the second test tube for supporting recovery or growth of a microorganism sample collected by use of the swab.

6. The assembly defined in claim 5, in which the swab is hydrated with a collection solution.

7. The assembly defined in claim 5, in which the first and second sides of the cap have internal threads, the open end portions of the first and second test tubes having external threads for coupling to either cap side in the manually detachable watertight fit.

8. The microbiological sampling kit defined in claim 7, in which the cap has an integral central hub section dividing the interior of the hollow shell into the first side and the second side and separating said sides from each other, the hub section having a first annular skirt extending close to but spaced from an interior surface of the shell in the first side thereof and constructed and arranged to engage and make sealing contact with the first test tube when coupled to the first side of the cap, the hub section having a second annular skirt extending close to but spaced from an interior surface of the shell in the second side thereof and constructed and arranged to engage and make sealing contact with the second test tube when coupled to the second side of the cap, said two skirts being coextensive for grasping by a user.

* * * * *